United States Patent
Kohlstruk et al.

(10) Patent No.: US 7,371,891 B2
(45) Date of Patent: *May 13, 2008

(54) MULTISTAGE CONTINUOUS PREPARATION OF CYCLOALIPHATIC DIISOCYANATES

(75) Inventors: Stephan Kohlstruk, Duelmen (DE); Manfred Kreczinski, Herne (DE); Hans-Werner Michalczak, Herne (DE)

(73) Assignee: Degussa AG, Duesseldorf (DE)

( * ) Notice: Subject to any disclaimer, the term of this patent is extended or adjusted under 35 U.S.C. 154(b) by 149 days.

This patent is subject to a terminal disclaimer.

(21) Appl. No.: 11/185,776

(22) Filed: Jul. 21, 2005

(65) Prior Publication Data

US 2006/0025626 A1    Feb. 2, 2006

(30) Foreign Application Priority Data

Jul. 28, 2004   (DE) ............... 10 2004 036 499

(51) Int. Cl.
*C07C 249/00* (2006.01)
*C07C 251/00* (2006.01)
*C07C 257/00* (2006.01)
*C07C 263/00* (2006.01)
*C07C 265/00* (2006.01)
*C07C 267/00* (2006.01)
*C07C 291/00* (2006.01)

(52) U.S. Cl. .................................... 560/336
(58) Field of Classification Search ........... 560/336, 560/330

See application file for complete search history.

(56) References Cited

U.S. PATENT DOCUMENTS

| | | | |
|---|---|---|---|
| 2,692,275 A | 10/1954 | Bortnick |
| 3,919,279 A | 11/1975 | Rosenthal et al. |
| 4,081,472 A | 3/1978 | Tsumura et al. |
| 4,268,683 A | 5/1981 | Gurgiolo |
| 4,386,033 A | 5/1983 | Koenig et al. |
| 4,692,550 A | 5/1983 | Tyler |
| 4,388,246 A | 6/1983 | Sundermann et al. |
| 4,530,796 A | 7/1985 | Mattner et al. |
| 4,596,678 A | 6/1986 | Merger et al. |
| 4,596,679 A | 6/1986 | Hellbach et al. |
| 4,713,476 A | 12/1987 | Merger et al. |
| 4,851,565 A | 7/1989 | Merger et al. |
| 5,087,739 A | 2/1992 | Bohmholdt et al. |
| 5,360,931 A | 11/1994 | Bohmholdt et al. |
| 5,386,053 A | 1/1995 | Otterbach et al. |
| 5,418,260 A | 5/1995 | Smith et al. |
| 5,453,536 A | 9/1995 | Dai et al. |
| 5,502,244 A | 3/1996 | Okawa et al. |
| 5,616,784 A | 4/1997 | Schwarz et al. |
| 5,646,328 A | 7/1997 | Deibele et al. |
| 5,744,633 A | 4/1998 | Wilmes et al. |
| 5,962,728 A | 10/1999 | Mason et al. |
| 6,204,409 B1 | 3/2001 | Aso et al. |
| 2005/0043561 A1 | 2/2005 | Kohlstruk et al. |
| 2005/0043562 A1 | 2/2005 | Kohlstruk et al. |
| 2005/0043563 A1 | 2/2005 | Kohlstruk et al. |

FOREIGN PATENT DOCUMENTS

| | | |
|---|---|---|
| DE | 1 022 222 | 1/1954 |
| DE | 196 27 552 A1 | 1/1998 |
| DE | 101 27 273 | 12/2002 |
| EP | 0 355 443 A2 | 2/1990 |
| EP | 0 566 925 A2 | 10/1993 |
| EP | 0 568 782 A2 | 11/1993 |

OTHER PUBLICATIONS

U.S. Appl. No. 11/100,603, filed Apr. 7, 2005, Kohlstruk et al.
U.S. Appl. No. 11/101,428, filed Apr. 8, 2005, Kohlstruk et al.

*Primary Examiner*—Yvonne Eyler
*Assistant Examiner*—Jennifer Y Cho
(74) *Attorney, Agent, or Firm*—Oblon, Spivak, McClelland, Maier & Neustadt, P.C.

(57) ABSTRACT

The invention relates to a multistage process for continuous and phosgene-free preparation of cycloaliphatic diisocyanates.

50 Claims, No Drawings

MULTISTAGE CONTINUOUS PREPARATION OF CYCLOALIPHATIC DIISOCYANATES

BACKGROUND OF THE INVENTION

1. Field of the Invention

The invention relates to a multistage process for continuous and phosgene-free preparation of cycloaliphatic diisocyanates.

2. Description of the Background

The synthetic access route to isocyanates may be via a series of different routes. The variant for industrial scale preparation of isocyanates which is the oldest and still predominates today is what is known as the phosgene route. This process is based on the reaction of amines with phosgene. A disadvantage of the phosgene process is the use of phosgene which, as a consequence of its toxicity and corrosivity, places particularly high requirements on its handling on the industrial scale.

There are several processes which avoid the use of phosgene for preparing isocyanates on the industrial scale. The term phosgene-free process is frequently used in connection with the conversion of amines to isocyanates using alternative carbonylating agents, for example urea or dialkyl carbonate (U.S. Pat. No. 4,713,476; U.S. Pat. No. 5,087,739; U.S. Pat. No. 4,268,683; and U.S. Pat. No. 6,204,409).

The urea route is based on the urea-mediated conversion of diamines to diisocyanates via a two-stage process. In the first step, a diamine is reacted with alcohol in the presence of urea or urea equivalents (for example alkyl carbonates, alkyl carbamates) to give a diurethane which typically passes through an intermediate purification stage and is then thermally cleaved in the second step to diisocyanate and alcohol (U.S. Pat. No. 5,087,739; U.S. Pat. No. 4,713,476; and U.S. Pat. No. 5,386,053). Alternatively, the actual urethane formation may also be preceded by the separate preparation of a diurea by selectively reacting the diamine with urea (U.S. Pat. No. 5,360,931). Also conceivable is a two-stage sequence consisting of partial reaction of urea with alcohol in the first and subsequent metering in and urethanization of the diamine in the second step (U.S. Pat. No. 5,744,633).

The thermal cleavage of urethanes to the corresponding isocyanates and alcohols has been known for some time and can be carried out either in the gas phase at high temperatures or at relatively low temperatures in the liquid phase. However, a problem in both procedures is that the thermal stress inevitably also causes undesired side reactions to take place which firstly reduce the yield and secondly lead to the formation of resinifying by-products which considerably disrupt the course of an industrial process as a result of deposits and blockages in reactors and workup apparatus.

There has therefore been no shortage of suggestions of chemical and process technology measures to achieve yield improvements and limit the undesired by-product formation. For instance, a series of documents describes the use of catalysts which accelerate the cleavage reaction of the urethanes (DE 10 22 222; U.S. Pat. No. 3,919,279; and U.S. Pat. No. 4,081,472). Indeed, it is entirely possible in the presence of suitable catalysts, which are a multitude of basic, acidic and also organometallic compounds, to increase the isocyanate yield in comparison to the uncatalyzed variant. However, the formation of undesired by-products can also not be prevented by the presence of a catalyst. The same applies to the additional use of inert solvents, as recommended in U.S. Pat. No. 3,919,279 and U.S. Pat. No. 4,081,472, in order to ensure uniform distribution of the heat supplied and of the catalyst in the reaction medium. However, the use of solvents boiling under reflux fundamentally has the consequence of a reduction in the space-time yield of isocyanates and is additionally hindered with the disadvantage of additional high energy demands.

Examples which are cited in U.S. Pat. No. 4,386,033 for thermal catalyzed cleavage of monourethanes describe the partial discharge of the reaction mixture to remove resinifying by-products formed in the course of the urethane cleavage. This procedure serves to prevent deposits and blockages in reactors and workup units. There are no indications which point to a yield-increasing utilization of the partial discharge. U.S. Pat. No. 4,388,246 describes a similar approach to a solution, in which the thermolysis is in this case carried out in the presence of solvents whose purpose is apparently to better absorb the involatile by-products. Here also, the partial discharge is not utilized for the purposes of yield optimization.

U.S. Pat. No. 5,087,739 discloses that a yield increase can be achieved when the higher molecular weight by-products which can and cannot be utilized and are formed in the cleavage reactor during the cleavage of diurethanes, to ensure a disruption-free and selective reaction, are discharged substantially continuously out of the reactor and subsequently converted for the most part in the presence of alcohol and then recycled into the diurethane preparation. The procedure described is associated with high energy demands, since nonutilizable by-products are removed from the effluent of the diurethane preparation by distillation, and all of the diurethane has to be evaporated. In contrast to U.S. Pat. No. 5,087,739, the urethanization effluent in the process of U.S. Pat. No. 5,386,053 is divided into two substreams of which only one is freed by distillation of its high-boiling, nonutilizable by-products, before the combined diurethane streams are fed to the deblocking reaction in the cleavage reactor. In addition, the continuous cleavage reactor discharge in U.S. Pat. No. 5,386,053 is recycled directly, i.e. without a reurethanization step, into the diurethane synthesis.

The preparation of the diurethanes in a one-pot reaction from urea, diamine and alcohol with simultaneous removal of ammonia is common practice and is described in a series of patents (U.S. Pat. No. 4,713,476; U.S. Pat. No. 5,087,739; and U.S. Pat. No. 5,386,053). A disadvantage is that the simultaneous reaction of urea, alcohol and diamine inevitably forms by-products in a relatively large amount, which impair the selectivity of the reaction and which have to be removed before the thermal deblocking of the diurethanes. U.S. Pat. No. 5,360,931 therefore claims a continuous process for preparing (cyclo)aliphatic diisocyanates which comprises essentially three main steps, of which the first describes the formation of bisureas, the second the formation of diurethanes from the bisureas and the third the cleavage of the diurethanes in the liquid phase to the desired diisocyanates—i.e. the diurethane is prepared in two separate stages. According to the teaching of U.S. Pat. No. 5,360,931, the effluent of the reaction sequence from bisurea formation and subsequent diurethane synthesis is initially freed distillatively of low and medium boilers such as alcohols, carbamates and carbonates, and the high boilers in the diurethane are removed afterward by short-path evaporation. The diurethane is deblocked thermally and a portion of the cleavage residue is discharged continuously, reurethanized with alcohol and recycled back into the diurethane synthesis stage.

It has been found that, surprisingly, when cycloaliphatic diamines are used, it is advantageous to prepare the cycloaliphatic diurethanes by two-stage reaction, which thus proceeds via bisurea, of cycloaliphatic diamines with alcohol and urea, to free them, to thermally cleave the cycloaliphatic diurethanes purified in this way to release the desired cycloaliphatic diisocyanate, to continuously discharge a portion of the cleavage residue from the cleavage apparatus and to reurethanize with alcohol to remove high boiler components therefrom, and to recycle the reurethanized stream purified in this way into the process. It has been found that this method firstly realizes a comparatively low steady-state concentration of high boiler components over the entire sequence of diurethane synthesis, diurethane purification and diurethane cleavage, so that deposits, which are promoted in particular by the high boiler components which are highly viscous by nature, can be substantially avoided, and also ensures good plant availability and good process yield even in the long term. Secondly, the sequence of reurethanization and high boiler removal downstream of the thermal cleavage reaction has the advantage that, in comparison to the customary procedure in which the high boilers are removed before the diurethane cleavage, the amount of diurethane to be converted to the vapor phase is significantly reduced, which allows capital and energy costs to be reduced.

SUMMARY OF THE INVENTION

The invention provides a multistage process for continuously preparing cycloaliphatic diisocyanates, by reacting cycloaliphatic diamines with carbonic acid derivatives and alcohols to give cycloaliphatic diurethanes and subsequently thermally cleaving the diurethanes to give cycloaliphatic diisocyanates, which comprises performing the formation of the diurethanes in two stages, cleaving the diurethane freed of low and medium boilers to release the desired diisocyanate, continuously discharging a portion of the cleavage residue from the cleavage apparatus, reurethanizing the discharge with alcohol, removing the high boiler components therefrom and recycling the reurethanized stream into the process.

The invention also provides a multistage process for continuously preparing cycloaliphatic diisocyanates of the formula (I)

OCN—R—NCO              (I)

where R is a bivalent cycloaliphatic hydrocarbon radical having from 4 to 18, preferably from 5 to 15, carbon atoms, with the proviso that the two isocyanate groups are bonded directly to a hydrocarbon cycle and at least 3 carbon atoms are disposed between them, by reacting cycloaliphatic diamines with carboxylic acid derivatives and alcohols to give diurethanes and thermally cleaving them, wherein a) cycloaliphatic diamines of the formula (II)

H$_2$N—R—NH$_2$              (II)

where R is a bivalent cycloaliphatic hydrocarbon radical having from 4 to 18, preferably from 5 to 15, carbon atoms, where the two nitrogen atoms are bonded directly to at least one hydrocarbon cycle and at least 3 carbon atoms are disposed between them, are reacted with urea and in the presence of alcohols of the formula (III)

R$^1$—OH              (III)

where R$^1$ is a radical as remains after removal of the hydroxyl group from a primary or secondary (cyclo)aliphatic alcohol having from 3 to 8 carbon atoms, in the absence or presence of catalysts to give cycloalkylenebisureas of the formula (IV)

H$_2$N—OC—NH—R—NH—CO—NH$_2$              (IV)

where R is a divalent cycloaliphatic hydrocarbon radical having from 4 to 18, preferably from 5 to 15, carbon atoms, with the proviso that the two nitrogens atoms flanking R are bonded directly to a hydrocarbon cycle and at least 3 carbon atoms are arranged between them, and the ammonia which is formed is removed simultaneously;

b) the resulting crude cycloalkylenebisurea is converted in a second reactor using the alcohol of the formula (III) used as a solvent in a), while continuously driving out the ammonia released, to cycloalkylenediurethane of the formula (V)

R$^1$O—OC—HN—R—NH—CO—OR$^1$              (V);

c) the alcohol, the dialkyl carbonates and/or alkyl carbamates are removed from the resulting reaction mixture and the alcohol is recycled in reaction stage a);

d) a removal of any high-boiling residues present in the resulting reaction mixture is fully or partially dispensed with;

e) the reaction mixture comprising the diurethanes purified by steps c) and d) is thermally cleaved in the presence of a catalyst continuously and without solvent, at temperatures of from 180 to 280° C., preferably from 200 to 260° C., and under a pressure of from 0.1 to 200 mbar, preferably from 0.2 to 100 mbar, in such a way that a portion of the reaction mixture of from 10 to 60% by weight based on the feed, preferably from 15 to 45% by weight based on the feed, is constantly discharged from the bottom;

f) the cleavage products are separated by rectification into crude diisocyanate and alcohol;

g) the crude cycloaliphatic diisocyanate, purified by distillation, and the pure product fraction are isolated;

h) the bottoms discharge from e) is reacted partially or fully with the alcohol from f) in the presence or absence of catalysts within from 1 to 150 min, preferably from 3 to 60 min, at temperatures of from 20 to 200° C., preferably from 50 to 170° C., and at a pressure of from 0.5 to 20 bar, preferably from 1 to 15 bar, the molar ratio of NCO groups to OH groups being up to 1:100, preferably 1:20 and more preferably 1:10;

i) the material-of-value stream from h) is separated into a material-of-value stream and a waste stream, and the waste stream which is rich in high boiler components is discharged from the process and disposed of;

j) a portion of the bottoms fraction of the purification by distillation g) is continuously discharged and conducted into the cleavage reaction e) or into the urethanization stage h);

k) optionally, the top fraction obtained in the purification distillation of the crude cycloaliphatic diisocyanate is likewise recycled into the urethanization stage h);

l) the purified reurethanized stream from i) is recycled into stages b) and/or c) or e).

DETAILED DESCRIPTION OF THE INVENTION

In the process according to the invention, cycloaliphatic diisocyanates can be prepared continuously, without any problem and in a very good yield. What is advantageous in the multistage process according to the invention is in particular the fact that even when cycloaliphatic diamines of the formula (II) are used as a starting material for the continuous diisocyanate synthesis, deposits, which are supported in particular by the high boiler components which are highly viscous by nature, can be substantially prevented and good plant availability and good process yield are ensured even in the long term. It is a further advantage of the multistage process according to the invention that it allows the amount of the diurethane to be converted to the vapor phase to be reduced to a minimum and in this way restricts the necessary energy demands.

To prepare the cycloalkylenebisureas of the formula (IV) in reaction stage a), the cycloaliphatic diamines of the formula (II) are reacted with urea in the presence of an alcohol of the formula (III), if desired also mixtures of such alcohols, in a reactor at from 100 to 145° C. and a pressure of from 0.7 to 1.8 bar, in the course of which the ammonia formed is driven out continuously. The reaction is effected preferably in a distillation reactor, in which case the reactants are introduced in a molar ratio of diamine:urea:alcohol of 1:2.0 to 2.4:3 to 10 continuously to the uppermost tray and the ammonia released is driven out by alcohol vapours which are introduced in the bottom of the distillation reactor. The required residence time is from 4 to 10 hours, preferably from 5 to 9 hours. The amount of alcohol introduced in the bottom to drive out the ammonia is from 0.05 to 3 kg/kg, preferably from 0.1 to 1 kg/kg, of bisurea, and the amount of alcohol thus introduced is drawn off at the top together with ammonia formed, freed of residual ammonia after partial condensation in an alcohol recovery column, and recycled into the bottom.

The crude cycloalkylenebisurea dissolved in alcohol which is obtained in the bottom of the distillation reactor is conducted continuously into a second reactor in which the conversion to the diurethane is effected at elevated temperature and elevated pressure, in the course of which ammonia is again released, and has to be removed from the reaction mixture for reasons of chemical equilibrium. The crude cycloalkyleneurea from a) is reacted further preferably in a pressure distillation reactor and at a molar ratio of bisurea to alcohol of from 1:5 to 12. The stream from a) is conducted preferably continuously to the uppermost tray of the pressure distillation reactor. The reaction takes place in the absence or presence of catalysts at reaction temperatures of from 140 to 270° C., preferably from 160 to 250° C., and under a pressure which is from 5 to 20 bar, preferably from 7 to 15 bar, within from 2 to 20 hours, preferably from 8 to 15 hours. The continuous driving-out of the ammonia released is promoted by alcohol vapours which are introduced in the bottom of the pressure distillation reactor and are appropriately generated in an evaporator mounted at the bottom of the column.

To increase the reaction rate, the diurethanes may be prepared in the presence of catalysts. Suitable catalysts are inorganic or organic compounds which contain one or more, preferably a cation of, metals or Groups 1-15, in accordance with the IUPAC-recommended Periodic Table of the Elements; for example halides such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates. Examples include the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Examples of typical catalysts include the following compounds: lithium ethoxide, lithium butoxide, sodium methoxide, potassium tert-butoxide, magnesium ethoxide, calcium methoxide, tin(II) chloride, tin(IV) chloride, lead acetate, aluminum trichloride, bismuth trichloride, copper(II) acetate, copper(II) chloride, zinc chloride, zinc octoate, titanium tetrabutoxide, vanadium trichloride, vanadium acetylacetonate, manganese(II) acetate, iron(II) acetate, iron (III) acetate, iron oxalate, cobalt chloride, cobalt naphthenate, nickel chloride, nickel naphthenate and mixtures thereof. The catalysts may optionally also be used in the form of their hydrates or ammoniates.

Starting compounds for the process according to the invention are diamines of the formula (II) which has already been mentioned above, alcohols of the formula (III) which has already been mentioned above, and also urea. Suitable diamines of the formula (II) are, for example, 1,4-diaminocyclohexane, 4,4'-dicyclohexylmethanediamine, 2,4-dicyclohexylmethanediamine, 2,2'-dicyclohexylmethanediamine and isomeric cycloaliphatic diamines, and also perhydrogenated diphenylmethanediamine. As a result of the preparation, diphenylmethanediamine (MDA) occurs as an isomer mixture of 4,4'-, 2,4- and 2,2'-MDA (see, for example, DE 101 27 273). Perhydrogenated diphenylmethanediamine is obtained by fully hydrogenating MDA and is accordingly a mixture of isomeric dicyclohexylmethanediamines ($H_{12}$MDA), i.e. 4,4'-, 2,4- and 2,2'-$H_{12}$MDA and possibly small amounts of (semi)aromatic MDA which has not been fully converted. The diamines of the formula (II) used are preferably 4,4'-dicyclohexylmethanediamine, 2,4-dicyclohexylmethanediamine and 2,2'-dicyclohexylmethanediamine, and also any mixtures of at least two of these isomers. It will be appreciated that diamines may also be used which deviate from the formula (II). Examples include 1,3- and 1,4-diaminomethylcyclohexane, 1,6-hexanediamine, 2,2,4- or 2,4,4-trimethyl-1,6-hexanamine and 3-aminomethyl-3,5,5-trimethylcyclohexylamine. However, preference is not given to using amines which deviate from the formula (II).

Suitable alcohols of the formula (III) are any aliphatic or cycloaliphatic alcohols which have a boiling point below 190° C. under atmospheric pressure. Examples include C1-C6-alkanols, for example methanol, ethanol, 1-propanol, 1-butanol, 2-butanol, 1-hexanol or cyclohexanol. The alcohol used is preferably 1-butanol.

In the course of the conversion of the reaction mixture, ammonia is released, whose removal from the reaction equilibrium has been found to be advantageous. When ammonia is discharged from the reactor, care has to be taken that the wall temperatures of the reactor and of the discharge tube are above 60° C., so that deposition of ammonium carbamate, which is formed in minimal amounts from ammonia and carbon dioxide by decomposition of urea, can be prevented. It has been found to be useful, for example, to carry out the reaction in a pressure distillation reactor, in which case the reaction mixture is conducted in countercurrent to alcohol vapors introduced in the bottom and in this way such intensive mixing of the liquid proceeds on the trays that they each virtually correspond to a battery stage. The vaporous mixture of alcohol and ammonia which is withdrawn at the top may, preferably under the pressure of the pressure distillation reactor and without condensing it beforehand, be conducted into a distillation column, to obtain alcohol free from ammonia. The alcohol is recycled into the bottom of the pressure distillation reactor and of the column. In order to prevent fouling of the reflux condenser with ammonium carbamate, an appropriate proportion of alcohol is permitted therein to set the temperature at the top to at least 60° C.

c) The excess alcohol, the dialkyl carbonates, if they have been formed, or alkyl carbamates or mixtures of at least two of these components are removed in one stage or advantageously in two stages. At the first stage, the reaction mixture is decompressed from the pressure level of reaction stage b) to a pressure of from 1 to 500 mbar, preferably from 2 to 150 mbar, and in this way separated into gaseous vapors which contain the predominant amount of alcohol and also any dialkyl carbonates and/or alkyl carbamates, and into a liquid effluent. In the second stage, the liquid effluent is freed of any remaining residual butanol and also medium boilers such as dialkyl carbonates and/or alkyl carbamates by thin-film evaporation at from 180 to 250° C., preferably from 200 to 230° C., and a pressure of from 0.1 to 20 mbar, preferably from 1 to 10 mbar, so that the residue consists substantially of the monomeric diurethane and in some cases high-boiling oligomers. The vapors may, after further distillative purification, be recycled into reaction stage a). Recycling of the dialkyl carbonates and/or alkyl carbamates into reaction stage b) is possible but not necessary.

d) Preference is given to dispensing with any removal of any high boilers present in the reaction mixture from stage c). However, if the separation described under i) of the reurethanized stream from stage h) is carried out only with one substream, i.e. partially, it may be advantageous to follow the routes for high boiler removal which are described below:

Optionally, the liquid stream from step c) which contains the monomeric diurethanes and any high-boiling oligomers and is obtained after the removal of low and medium boilers may be separated, preferably with the aid of a thin-film or short-path evaporator, at a temperature of from 180 to 270° C., preferably from 200 to 250° C., and under a pressure of from 0.01 to 10 mbar, preferably from 0.02 to 5 mbar, by distillation into a material-of-value stream which contains the monomeric diurethanes and the lower-boiling by-products and a nondistillable by-product stream. The nondistillable by-product stream which contains the high-boiling components is discharged from the preparative process and is typically discarded as a residue whose material cannot be utilized.

Optionally, the stream from stage c) which contains any high-boiling oligomers, before its above-described distillative purification, may also be divided into two substreams of which one is fed directly to the deblocking reaction (see e)) and the other initially passes through the high boiler removal just described.

e) The material-of-value stream from stage c) and optionally from stage d) which contains the monomeric diurethanes and the lower-boiling by-products is partly and continuously thermally cleaved in a suitable apparatus, without solvents in the liquid phase in the presence of catalysts at temperatures of from 180 to 280° C., preferably from 200 to 260° C., and under a pressure of from 0.1 to 200 mbar, preferably from 0.2 to 100 mbar. The conversion of diurethane to diisocyanate in the apparatus for thermal cleavage may, depending on the diurethane used, be selected substantially freely and is typically within the range of from 10 to 95% by weight, preferably from 35 to 85% by weight of the diurethane feed. The uncleaved proportion of the reaction mixture which contains unconverted diurethanes, high-boiling by-products and other reutilizable and nonutilizable by-products is continuously discharged. The amount of the discharge is governed, inter alia, by the desired conversion and the desired capacity of the cleavage reaction and can be easily determined experimentally. It is typically from 10 to 60% by weight, preferably from 15 to 45% by weight, based on the feed.

Useful catalysts for chemically cleaving the diurethanes are, for example, the aforementioned inorganic and organic compounds which catalyze urethane formation. Preference is given to using chlorides of zinc, tin, or copper, and also zinc oxides, manganese oxides, iron oxides or cobalt oxides, in which case the catalyst is metered into the stream from the purification stage c) and optionally d), before it is fed into the cleavage, as a from 0.01 to 25% by weight, preferably from 0.05 to 10% by weight, solution or suspension, preferably into the alcohol which is also used for urethane preparation, in an amount of from 5 to 400 ppm, preferably from 10 to 100 ppm.

Suitable cleavage apparatus is, for example, cylindrical cleavage reactors, for example tubular furnaces or preferably evaporators such as falling-film, thin-film or bulk evaporators, selected from Robert evaporators, Herbert evaporators, Caddle-type evaporators, Oskar evaporators and heating cartridge evaporators.

In principle, the main concern is to keep the average residence time of isocyanate groups, which are inevitably released when the alcohol is deblocked, in the cleavage zone very low and thus to limit undesired side reactions to a minimum.

Preference is given to carrying out the cleavage in a combined cleavage and rectification column, which is equipped for the energy supply in the bottom with a falling-film evaporator, in the lower third with a unit for additional energy input or for energy recovery, in the upper third with a unit to remove preferably crude diisocyanate and at the top with a condenser for the reflux and the removal of pure alcohol.

f) The cleavage products which are formed in the thermal cleavage and are composed in particular of alcohol, diisocyanate and partially cleaved diurethanes are separated by rectification at from 95 to 260° C., preferably from 110 to 245° C., and a pressure of from 0.5 to 250 mbar, preferably from 1 to 100 mbar, into alcohol and into a crude diisocyanate mixture, consisting of cycloaliphatic diisocyanate, partially cleaved cycloaliphatic diisocyanate and in some cases small amounts of cycloaliphatic diurethane. This separation may be carried out, for example, in the cleavage column of the abovementioned combined cleavage and rectification column.

g) The crude mixture which is preferably obtained by rectification, consisting of cycloaliphatic diisocyanate, partially cleaved cycloaliphatic diurethane and in some cases small fractions of cycloaliphatic diurethane, is purified by distillation at a temperature of from 95 to 260° C., preferably from 110 to 245° C., and under a pressure of from 0.5 to 150 mbar, preferably from 1 to 75 mbar, and the resulting fractions are recycled or isolated as a pure product.

h) The bottoms discharge from the deblocking stage e) is recycled partially or fully with the alcohol from the rectification stage f), the molar ratio of NCO groups to OH groups being up to 1:100, preferably 1:20 and more preferably 1:10, and the reaction mixture is reacted in the presence or absence of catalysts, within from 1 to 150 min, preferably from 3 to 60 min, at temperatures of from 20 to 200° C., preferably from 50 to 170° C. and a pressure of from 0.5 to 20 bar, preferably from 1 to 15 bar. The reaction may be carried out in a continuous tank battery or in a tubular reactor. Useful catalysts are in principle any catalysts which promote the NCO/OH reaction. Examples include tin octoate, dibutyltin laurate, tin dichloride, zinc dichloride, copper chloride, copper dichloride, iron dichloride, iron trichloride and triethylamine.

i) The reurethanized stream from stage h) is separated into a material-of-value and a waste stream and the waste stream rich in high boiler components is discharged from the process and discarded. The two streams are separated preferably by distillation with the aid of a thin-film or short-path evaporator, at a temperature of from 180 to 270° C., preferably from 200 to 250° C., and under a pressure of from 0.01 to 10 mbar, preferably from 0.02 to 5 mbar. The material-of-value stream which comprises the monomeric diurethanes and the lower-boiling by-products is obtained as the distillate. The waste stream which is rich in high-boiling components is obtained as the residue and is discharged from the preparative process and typically discarded as a nonutilizable material. Alternatively, but not preferably, the separation into material-of-value and waste material may also be effected by extraction. An example of a suitable extractant is supercritical carbon dioxide.

Optionally, the reurethanized stream may also be divided into two substreams before the distillative purification described above, from which one is fed directly to the purification stage c). The two streams can be divided in a ratio of from 99:1 to 1:99, preferably from 99:5 to 5:95. Optionally, the reurethanized stream leading to the high boiler removal may initially be freed partly or fully of excess alcohol. This is preferably effected by distillation. The alcohol removed may be recycled as desired in stage a) and/or b).

j) A portion of the bottoms fraction of the purifying distillation g) is continuously discharged and optionally recycled into the deblocking stage e) or into the urethanization stage h). Preference is given to recycling into the urethanization stage. The amount of the discharge is from 0.1 to 50% by weight, preferably from 0.2 to 25% by weight, of the feed of crude diisocyanate into the purifying distillation stage.

k) The top fraction of the purifying distillation stage g) may be discarded or preferably recycled into the urethanization stage h). The amount of top fraction removed per unit time is from 0.1 to 3% by weight, preferably from 0.3 to 1% by weight, of the feed of crude diisocyanate into the purifying distillation.

l) The purified reurethanized stream from stage i) is recycled into the low and medium boiler removal c) and/or the diurethane preparation b) or the diurethane cleavage c).

The multistage process according to the invention for continuously preparing cycloaliphatic diisocyanates with recycling and discharge of the by-products allows, for distillable cycloaliphatic diisocyanates, a reaction which proceeds without disruption and with high selectivity to be ensured. The process according to the invention is suitable in particular for preparing cycloaliphatic diisocyanates having from 4 to 18, preferably from 5 to 15, carbon atoms, such as 1,4-diisocyanatocyclohexane, 4,4'-dicyclohexylmethane diisocyanate (4,4'-$H_{12}$MDI), 2,2'-dicyclohexylmethane diisocyanate (2,2'-$H_{12}$MDI), 2,4-dicyclohexylmethane diisocyanate (2,4-$H_{12}$MDI) or else mixtures of the aforementioned isomeric dicyclohexylmethane diisocyanates ($H_{12}$MDI), as are obtained, for example, by the nature of the conversion of perhydrogenated MDA to $H_{12}$MDI. Very particular preference is given to preparing 4,4'-dicyclohexylmethane diisocyanate, and also any mixtures of 4,4'-$H_{12}$MDI, 2,4-$H_{12}$MDI and 2,2'-$H_{12}$MDI.

The cycloaliphatic diisocyanates prepared are excellently suited to preparing polymers containing urethane, isocyanurate, amide and/or urea groups by the polyisocyanate polyaddition process. They additionally find use for preparing polyisocyanate mixtures modified with urethane, biuret and/or isocyanurate groups. Such polyisocyanate mixtures of cycloaliphatic diisocyanates are used in particular for preparing high-value, light-resistant polyurethane coatings.

For example, polymers containing urethane may be prepared by reacting the prepared cycloaliphatic disocyanates with at least one polyol. At least one polyol may be selected from known polyols usually used in the production of polyurethanes.

Known polyols are those compounds that include dihydric alcohols having 2 to 20 carbon atoms (aliphatic diols, for instance, alkylene glycols such as ethylene glycol, diethylene glycol, propylene glycol, 1,3- or 1,4-butanediol, 1,6-hexanediol, and neopentylglycol; and alicyclic diols, for instance, cycloalkylene glycols such as cyclohexanediol and cyclohexanedimethanol); trihydric alcohols having 3 to 20 carbon atoms (aliphatic triols, for instance, alkane triols such as glycerol, trimethylolpropane, trimethylolethane, and hexanetriol, and triethanolamine); polyhydric alcohols having 4 to 8 hydroxyl groups and 5 to 20 carbon atoms (aliphatic polyols, for instance, alkane polyols and intramolecular or intermolecular dehydration products of the same such as pentaerythritol, sorbitol, mannitol, sorbitan, diglycerol, and dipentaerythritol; and saccharides and derivatives of the same such as sucrose, glucose, mannose, fructose, and methylglucoside).

Other mentionable polyols include monocyclic polyhydric phenols such as pyrogallol, hydroquinone and phloroglucinol; bisphenols such as bisphenol A, bisphenol F and bisphenol sulfone; and condensation products of phenols and formaldehyde (novolak).

Additionally, the above-mentioned polyols may include oligomers or polymers of alkylene oxides having 2 to 8 carbon atoms. The alkylene oxides include ethylene oxide, propylene oxide, 1,2-, 1,4-, 1-3, or 2,3-butylene oxide, styrene oxide, and the like.

Moreover, the above-mentioned polyols may include co-oligomers or co-polymers of alkylene oxides having 2 to 8 carbon atoms; wherein the alkylene oxides include combinations of two or more of ethylene oxide, propylene oxide, 1,2-, 1,4-, 1-3, or 2,3-butylene oxide, styrene oxide in block addition and/or random addition. Preferably, propylene oxide or a combination of propylene oxide and ethylene oxide (containing not more than 25 mass % of ethylene) is used.

Other examples of polyols include, but are not limited to, for example, aminic polyols such as JEFFAMINE™ as described in U.S. Pat. No. 5,418,260.

Having generally described this invention, a further understanding can be obtained by reference to certain specific examples which are provided herein for purposes of illustration only, and are not intended to be limiting unless otherwise specified.

EXAMPLES

Example 1

Preparation According to the Invention of Dicyclohexylmethane Diisocyanate ($H_{12}$MDI) from Perhydrogenated Diphenylmethanediamine and Urea in the Presence of n-butanol Every hour, the uppermost tray of a distillation reactor was charged with 281.5 g of $H_{12}$MDA, 164.9 g of urea and 595 g of n-butanol, and the reaction mixture was boiled at atmospheric pressure, 135° C. and an average residence time of 8 hours while continuously removing the ammonia released. The solution, obtained in the bottom of the distillation reactor, of bisurea in butanol was preheated to 190° C. using a heat exchanger, conducted to the uppermost tray of a pressure distillation reactor and reacted further at from 11 to 14 bar, 220° C. and with an average residence time of 10.5 h. In the bottom of the pressure distillation reactor, 540.1 g of n-butanol per hour were fed in and the amount of alcohol drawn off at the top together with the ammonia released was selected such that it corresponded to the alcohol introduction in the bottom. The reactor effluent, together with the stream from the high boiler removal, was subsequently freed of excess alcohol, low boilers and medium boilers in the flash vessel at 55 mbar with subsequent thin-film evaporation at 220° C. and 2 mbar, and the remaining 771.1 g/h of bis(4-butoxycarbonylaminocyclohexyl)methane ($H_{12}$MDU) were conducted as a melt (140° C.) into the circulation of the falling-film evaporator of the cleavage and rectification column, and the deblocking reaction was carried out at a temperature of 239° C. and a bottom pressure of 10 mbar in the presence of a steady-state concentration of tin dichloride of 16 ppm. The cleavage gases, $H_{12}$MDI and butanol, were condensed out in two condensers connected in series at 85° C. and −25° C. The resulting about 97% crude $H_{12}$MDI was fed to a purifying distillation where 320.9 g/h of $H_{12}$MDI having a purity of >99.5% were obtained, which corresponds to a yield based on the amine of 92%. 228.9 g/h of butanol were obtained as the top product of the cleavage and rectification column. To maintain constant mass within the cleavage and rectification column and avoid fouling and blockages of the cleavage apparatus, a substream was continuously discharged from the circuit and, together with 23.7 g/h of bottoms discharge from the $H_{12}$MDI purifying distillation and the top product from the cleavage and rectification column, purified and reurethanized. The reurethanized stream was freed of excess butanol by flash evaporation at 40 mbar and separated by means of a short-path evaporator at 230° C. and a pressure of 0.04 mbar into a waste stream rich in high boilers and a material-of-value stream. The 229.9 g/h of material-of-value stream were fed to the flash vessel together with the reactor effluent of the diurethane preparation.

The present application claims the benefit of priority to German Patent Application No. 102004036499.0, filed Jul. 28, 2004; the entire contents of which are incorporated by reference.

Obviously, numerous modifications and variations of the present invention are possible in light of the above teachings. It is therefore to be understood that within the scope of the appended claims, the invention may be practiced otherwise than as specifically described herein.

The invention claimed is:

1. A multistage process for continuously preparing a cycloaliphatic diisocyanate, by reacting a cycloaliphatic diamine with a carbonic acid derivative and an alcohol to give a cycloaliphatic diurethane and subsequently thermally cleaving the cycloaliphatic diurethane to give a cycloaliphatic diisocyanate, which comprises:
performing the formation of the cycloaliphatic diurethane in two stages;
cleaving the cycloaliphatic diurethane freed of low and medium boilers to release the desired cycloaliphatic diisocyanate;
continuously discharging a portion of the cleavage residue from the cleavage apparatus;
reurethanizing the discharge with an alcohol;
removing the high boiler components therefrom; and
recycling the reurethanized stream into the process.

2. A multistage process for continuously preparing a cycloaliphatic diisocyanate of the formula (I)

OCN—R—NCO                    (I)

where R is a bivalent cycloaliphatic hydrocarbon radical having from 4 to 18 carbon atoms, with the proviso that the two isocyanate groups are bonded directly to a hydrocarbon cycle and at least 3 carbon atoms are disposed between them, by reacting a cycloaliphatic diamine with a carboxylic acid derivative and an alcohol to give a cycloaliphatic diurethane and thermally cleaving them, which comprises:

a) reacting a cycloaliphatic diamine of the formula (II)

$H_2N—R—NH_2$                    (II)

where R is a bivalent cycloaliphatic hydrocarbon radical having from 4 to 18 carbon atoms, where the two nitrogen atoms are bonded directly to at least one hydrocarbon cycle and at least 3 carbon atoms being disposed between them;
with urea in the presence of an alcohol of formula (III)

$R^1$—OH                    (III)

where $R^1$ is a radical as remains after removal of the hydroxyl group from a primary or secondary (cyclo) aliphatic alcohol,
in the absence or presence of catalysts to give cycloalkylenebisureas of the formula (IV)

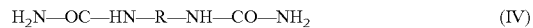

$H_2N—OC—HN—R—NH—CO—NH_2$                    (IV)

where R is a divalent cycloaliphatic hydrocarbon radical having from 4 to 18 carbon atoms, with the proviso that the two nitrogens atoms flanking R are bonded directly to a hydrocarbon cycle and at least 3 carbon atoms are arranged between them, and the ammonia which is formed is removed simultaneously and continuously;

b) converting a resultant cycloaliphatic bisurea in a second reactor using the alcohol of the formula (III) used as a solvent in a), while continuously driving out the ammonia released, to cycloaliphatic diurethane of the formula (V)

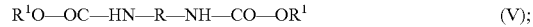

$R^1O—OC—HN—R—NH—CO—OR^1$                    (V);

c) removing the resultant alcohol, a dialkyl carbonate and/or an alkyl carbamate from the resultant reaction mixture, and recycling the alcohol into the reaction stage a);

d) fully or partially dispensing any high-boiling residues present in the resultant reaction mixture;

e) continuously and thermally cleaving the reaction mixture comprising the cycloaliphatic diurethane purified by steps c) and d) without solvent in the presence of a catalyst, at temperatures of from 180° C. to 280° C. and under a pressure of from 0.1 mbar to 200 mbar and constantly discharging a portion of the reaction mixture of from 10 wt % to 60 wt % based on the feed from the bottom;

f) separating by rectification the cleavage products into crude cycloaliphatic diisocyanate and alcohol;

g) isolating the crude cycloaliphatic diisocyanate, purified by distillation, and a pure product fraction;

h) reacting part or whole of the bottoms discharge from e) with the alcohol from f), in the presence or absence of catalysts, within from 1 min to 150 min at temperatures of from 20° C. to 200° C. and at a pressure of from 0.5 bar to 20 bar the molar ratio of NCO groups to OH groups being up to 1:100 to obtain a reurethanized stream;

i) separating the reurethanized stream from h) into a material-of-value stream and a waste stream, and j) discharging and discarding the waste stream comprising high boiler components from the process;

k) continuously discharging and conducting a portion of the bottoms fraction of the purification by distillation g) into the cleavage reaction e) or into the urethanization stage h);

l) optionally, recycling the top fraction obtained in the purification by distillation of the crude cycloaliphatic diisocyanate into the urethanization stage h);

m) recycling the purified reurethanized stream from i) into stage b), stage c), both stage b) and stage c), or stage e).

3. The multistage process of claim 1 or 2, wherein the cycloaliphatic diamine is selected from the group consisting of 4,4'-dicyclohexylmethanediamine, 2,4-dicyclohexylmethanediamine, 2,2'-dicyclohexylmethanediamine, and mixtures thereof.

4. The multistage process of claim 1 or 2, wherein the cycloaliphatic diamine is selected from the group consisting of 4,4'-dicyclohexylmethanediamine, an isomeric cycloaliphatic diamine, and mixtures thereof.

5. The multistage process of claim 1 or 2, wherein the cycloaliphatic diamine is 1,4-diaminocyclohexane.

6. The process of claim 2, wherein stage a) occurs in a reactor at from 100° C. to 145° C. and a pressure of from 0.7 bar to 1.8 bar.

7. The process of claim 2, wherein stage a) occurs in a distillation reactor.

8. The process of claim 2, wherein the reaction in stage a) has a molar ratio of diamine:urea:alcohol of from 1:2.0 to 2.4:3 to 10.

9. The multistage process of claim 2, wherein, in stage a), further comprises continuously supplying the reactants to an uppermost tray and
removing the ammonia by alcohol vapors which are introduced into the bottom of the distillation reactor.

10. The process of claim 2, wherein the residence time of the reactants in stage a) is from 4 hours to 10 hours.

11. The process of claim 2, wherein stage b) occurs in a pressure distillation reactor.

12. The process of claim 2, wherein stage b) has a molar ratio of bisurea to alcohol of 1:5 to 12.

13. The process of claim 2, which further comprises continuously conducting the stream from a) to the uppermost tray of the reactor of stage b).

14. The process of claim 2, wherein the reaction in stage b) occurs at a reaction temperature of from 140° C. to 270° C. and under a pressure which is from 5 bar to 20 bar.

15. The process of claim 2, wherein the reaction in stage b) occurs within from 2 hours to 20 hours.

16. The process of claim 2, wherein the reaction in stage a), stage b), or both stage a) and stage b) occurs in the presence of catalysts.

17. The process of claim 2, wherein, in stages a) and b), the alcohol has from 1 to 6 carbon atoms.

18. The process of claim 2, wherein, in stages a) and b), the alcohol is butanol.

19. The process of claim 2, wherein stage c) occurs in two stages.

20. The process of claim 19, wherein, the first stage comprises decompressing the reaction mixture from the pressure level of reaction stage b) to a pressure of from 1 mbar to 500 mbar.

21. The process of claims 19 or 20, wherein, a second stage comprises freeing the liquid effluent of any residual alcohol present and also of medium boilers comprising dialkyl carbonate, an alkyl carbamate or combinations thereof by thin-film evaporation at from 180° C. to 250° C. and a pressure of from 0.1 mbar to 20 mbar.

22. The process of claims 19, 20 or 21, which further comprises distillatively purifying the vapor of stage c) to obtain a purified vapor and feeding the purified vapor into reaction stage a).

23. The process of claim 2, wherein the separation in stage d) occurs at a temperature of from 180° C. to 260° C. and under a pressure of from 0.01 mbar to 10 mbar.

24. The process of claim 23, wherein the separation of stage d) occurs by means of a thin-film or short-path evaporator.

25. The process of claim 2, which further comprises discharging and discarding at least one by-product obtained from stage d).

26. The process of claim 2, which further comprises
dividing the stream of stage c) before it is transferred to stage d), into two substreams and
directly feeding one of the two substreams to the deblocking reaction of stage e).

27. The process of claim 2, wherein the thermally induced diurethane cleavage of stage e) occurs in a tubular furnace.

28. The process of claim 2, wherein stage e) occurs in a combined cleavage and rectification column.

29. The process of claim 2, wherein, in stage e), thermal cleavage continuously occurs in the presence of catalysts at temperatures of from 180° C. to 280° C. and under a pressure of from 0.1 mbar to 200 mbar.

30. The process of claim 2, wherein, in stage e), cleavage occurs in the absence of solvent in the liquid phase.

31. The process of claim 2, wherein stage e) occurs in the presence of catalysts.

32. The process of claim 2, wherein, in stage e), the conversion of cycloaliphatic diurethane to cycloaliphatic diisocyanate is selected freely depending on the cycloaliphatic diurethane used.

33. The process of claim 1, which further comprises
continuously discharging, in stage e), a portion of the reaction mixture which comprises unconverted cycloaliphatic diurethane, high-boiling by-products and other reutilizable and nonutilizable by-products.

34. The process of claim 33, wherein the amount of the discharge is from 10 wt % to 60 wt %.

35. The process of claim 2, wherein stage f) occurs in a combined cleavage and rectification column.

36. The process of claim 2, wherein operation occurs at temperatures of from 95° C. to 260° C. and a pressure of from 0.5 mbar to 250 mbar.

37. The process of claim 2, wherein, in stage g), further comprises purifying by distillation the crude fraction obtained from stage f), which comprises the cycloaliphatic diisocyanate, partially cleaved cycloaliphatic diurethane, and optionally a small fraction of cycloaliphatic diurethane, at a temperature of from 95° C. to 260° C. and under a pressure of from 0.5 mbar to 150 mbar.

38. The process of claim 2, which further comprises
isolating the pure product fraction obtained in stage g) or recycling the pure product fraction obtained in stage g) into stage h).

39. The process of claim 2, wherein, in stage i), operation occurs at a temperature of from 180° C. to 270° C. and under a pressure of from 0.01 mbar to 10 mbar.

40. The process of claim 2, wherein stage i) occurs by extraction.

41. The process of claim 2, which further comprises
dividing the reurethanized stream in stage i), before the distillative purification, into two substreams, and
directly feeding one of the two substreams to the purification stage c).

42. The process of claim 41, wherein the two substreams are divided in a ratio of from 99:1 to 1:99.

43. The process of claim 2, wherein stage i) occurs in a continuous tank battery or in a tubular reactor.

44. The process of claim 2, wherein the reaction in stage h) occurs in the presence of catalysts selected from the group consisting of a tin carboxylate, a zinc carboxylate, a copper carboxylate, a tin halide, a zinc halide, a copper halide, a tertiary amine, an iron halide, and combinations thereof.

45. The process of claim 2, wherein, continuously discharging and conducting of the portion of the bottoms fraction in stage j), comprises recycling into the deblocking stage e) or into the urethanization stage h).

46. The process of claim 45, wherein, in stage j), the amount of the discharge is from 0.1 wt % to 50 wt % of the feed of crude polyisocyanate into the purifying distillation stage.

47. The process of claim 2, which further comprises
freeing a part or a whole amount of alcohol contained in the reurethanized stream from h) leading to the high boiler removal i) to obtain a freed alcohol and
recycling the freed alcohol into stage a), stage c) or both stage a) and stage c).

48. A process of claim 2, which further comprises
freeing a part or a whole amount of alcohol contained in the reurethanized stream from h) leading to the high boiler removal i) to obtain a freed alcohol and
recycling the freed alcohol into stage b), stage c), both stage b) and stage c), or stage e).

49. The process of claim 1 or claim 2, wherein the cycloaliphatic diisocyanate is selected from the group consisting of 1,4-diisocyanatocyclohexane, 4,4'-dicyclohexylmethane diisocyanate, 2,2'-dicyclohexylmethane diisocyanate, 2,4-dicyclohexylmethane diisocyanate, any mixture of at least two isomeric dicyclohexylmethane diisocyanates.

50. The process of claim 1 or claim 2, wherein the cycloaliphatic diamine is selected from the group consisting of 1,3-diaminomethylcyclohexane, 1,4-diaminomethylcyclohexane, 1,6-diaminocyclohexane, 2,2,4-trimethylcyclohexane-1,6-diamine, 2,4,4-trimethylcyclohexane-1,6-amine, and 3-aminomethyl-3,5,5-trimethylcyclohexylamine.

* * * * *